(12) United States Patent
Eum et al.

(10) Patent No.: US 8,506,809 B2
(45) Date of Patent: Aug. 13, 2013

(54) METHOD AND APPARATUS FOR PRODUCING BIO-GAS EMPLOYING TECHNOLOGY FOR IMPROVING QUALITY OF RAW MATERIAL FED THERETO

(75) Inventors: Young Jin Eum, Gyeonggi-do (KR); Gi Yang Oh, Seoul (KR); Jang Gyu Kim, Gyeongbuk (KR); Hun Suk, Gyeonggi-do (KR); Myeong Jung Yu, Seoul (KR); Long Li, Seoul (KR)

(73) Assignee: Boo Kang Tech Co., Ltd., Seoul (KR)

( * ) Notice: Subject to any disclaimer, the term of this patent is extended or adjusted under 35 U.S.C. 154(b) by 317 days.

(21) Appl. No.: 13/064,529

(22) Filed: Mar. 30, 2011

(65) Prior Publication Data

US 2011/0297613 A1    Dec. 8, 2011

(30) Foreign Application Priority Data

Jun. 4, 2010    (KR) ........................ 10-2010-0053086

(51) Int. Cl.
*C02F 3/28*    (2006.01)
*C02F 11/04*    (2006.01)

(52) U.S. Cl.
USPC .......................................... 210/603; 210/259

(58) Field of Classification Search
USPC ......................................... 210/603, 252, 259
See application file for complete search history.

(56) References Cited

U.S. PATENT DOCUMENTS 3,226,317 A * 12/1965 Albertson ..................... 210/609
3,394,814 A *  7/1968 Albertson .................. 210/195.3
3,464,918 A *  9/1969 Grant ............................ 210/605

FOREIGN PATENT DOCUMENTS

| DE | 19937876 A1 | * 3/2001 |
| JP | 9-271794 A | 10/1997 |
| JP | 11-319826 A | 11/1999 |
| JP | 2005-95729 A | 4/2005 |
| KR | 10-0745186 B1 | 7/2007 |
| WO | WO 88/04282 A1 | * 6/1988 |

OTHER PUBLICATIONS

International Search Report, from the Korean Patent Office, issued in counterpart International Application No. PCT/KR2011/002102, mailed Dec. 15, 2011.

* cited by examiner

*Primary Examiner* — Fred Prince
(74) *Attorney, Agent, or Firm* — Stites & Harbison PLLC; Juan Carlos A. Marquez, Esq.

(57) ABSTRACT

Disclosed are a method and an apparatus for production of bio-gas, capable of improving quality of a raw material to be fed thereto. Among the raw material, a part free from inhibitory materials is directly introduced an anaerobic digestion reactor while the other part containing the inhibitory materials is introduced into a first solid-liquid separator and separated into a solid-phase material free from the inhibitory materials and a liquid-phase material containing the inhibitory materials. The solid-phase material in the first solid-liquid separator is fed to the anaerobic digestion reactor after hydrolysis. A liquid waste in the anaerobic digestion reactor and a liquid-phase material in the first solid-liquid separator are concentrated by a sludge concentrator. Through solid-liquid separation of the raw material, only a solid-phase sludge removed from the inhibitory materials is fed to the anaerobic digestion reactor, thereby suitably maintaining desired activity of microorganisms used for producing bio-gas.

3 Claims, 1 Drawing Sheet

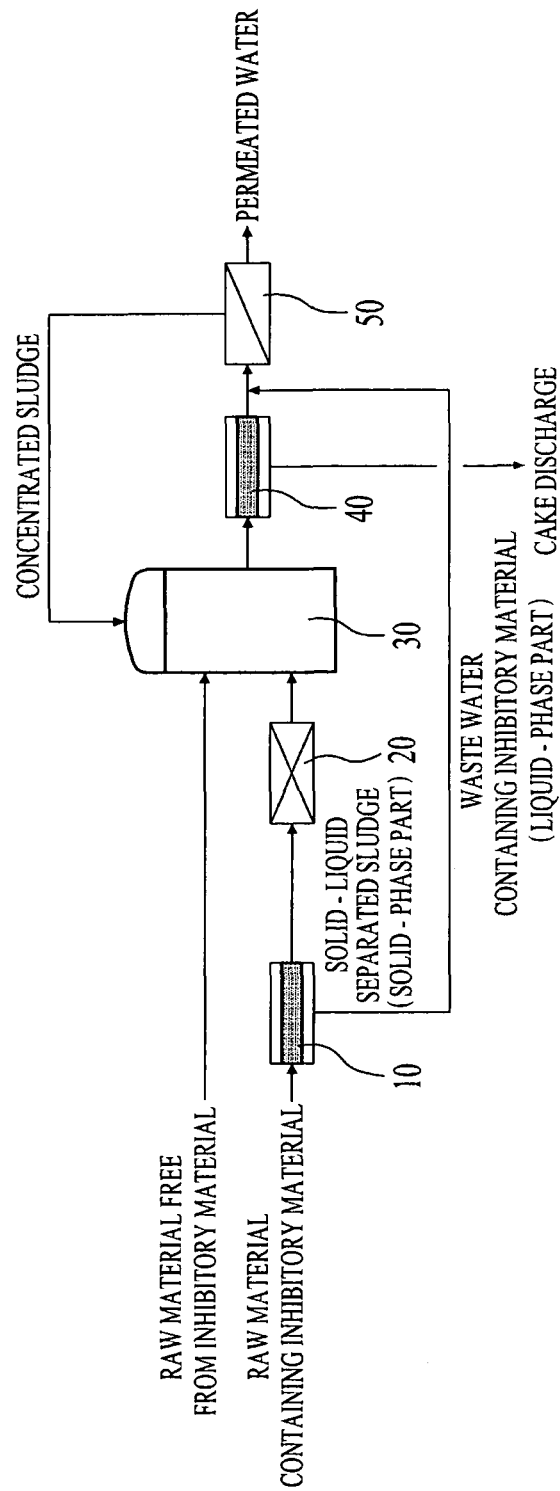

METHOD AND APPARATUS FOR PRODUCING BIO-GAS EMPLOYING TECHNOLOGY FOR IMPROVING QUALITY OF RAW MATERIAL FED THERETO

RELATED APPLICATIONS

This application claims priority from Korean Patent Application No. 10-2010-0053086, filed on Jun. 24, 2010 in the Korean Intellectual Property Office, the entire disclosure of which is incorporated herein by reference.

BACKGROUND OF THE INVENTION

1. Field of the Invention

The present invention relates to a method and an apparatus for production of bio-gas employing a specific technology for improving quality of a raw material fed thereto.

2. Description of the Related Art

In production of bio-gas, organic waste and bio-mass are generally used as main raw materials. However, such main raw materials include a great amount of inhibitory materials (such as ammonia, sulfides, salt, heavy metals, etc.) that deteriorate activity of microorganisms used for producing bio-gas, depending on kinds of the organic waste. These inhibitory materials are mostly present as dissolved matters (in a liquid state) in water, while not existing in a solid portion.

When an organic waste (solid and/or liquid phase) is directly introduced into an anaerobic digestion reactor, inhibitory materials in the liquid-phase of the organic waste deteriorate activity of microorganisms and considerably decrease bio-gas productivity, in turn causing the digestion reactor to be shut-down. In addition, since an organic waste in a solid-phase is fed into the anaerobic digestion reactor, it requires a long residence time in order to decompose the organic waste and causes problems such as increase in a capacity of the digestion reactor and/or equipment costs.

Meanwhile, owing to a slow growth of anaerobic microorganisms, they must reside in an anaerobic digestion reactor for a long term during anaerobic digestion, in order to maintain a desired amount of microorganisms to thereby maximize an amount of bio-gas to be generated. However, a typical anaerobic digestion reactor has a relatively small capacity and does not allow microorganisms to reside therein for a long term, thus not ensuring a desired amount of the microorganisms. As a result, an amount of bio-gas to be generated may be decreased, in turn encountering malfunction or loss of function of the anaerobic digestion reactor.

SUMMARY OF THE INVENTION

Therefore, in order to overcome the foregoing problems of conventional art, an object of the present invention is to provide a method and an apparatus for production of bio-gas, which includes introducing only a solid-phase sludge into an anaerobic digestion reactor, after removing inhibitory materials from a raw material to be fed thereto, through solid-liquid separation, to thereby appropriately maintain desired activity of microorganisms generating the bio-gas.

In order to accomplish the above object, there is provided an apparatus for producing bio-gas according to the present invention, including: an anaerobic digestion reactor to which a part of a raw material is fed, wherein the part does not contain inhibitory materials; a first solid-liquid separator to which the other part of the raw material is fed, wherein the other part contains the inhibitory materials, and which separates this part into a solid-phase material free from the inhibitory materials and a liquid-phase material containing the inhibitory materials; a hydrolysis reactor that executes hydrolysis of the solid-phase material obtained from the first solid-liquid separator and then feeds the treated material into the anaerobic digestion reactor; and a sludge concentrator that concentrates the liquid-phase material obtained from the first solid-liquid separator as well as a liquid waste (a leachate) of the anaerobic digestion reactor.

Preferably, the foregoing apparatus further includes a second solid-liquid separator to execute solid-liquid separation of a digested waste fed from the anaerobic digestion reactor in order to feed the liquid-phase material to the sludge concentrator.

According to the present invention, there is also provided a method for producing bio-gas, including: (a) separating a part of a raw material, which contains inhibitory materials, into a solid-phase material free from the inhibitory materials and a liquid-phase material containing the inhibitory materials; (b) hydrolyzing the solid-phase material generated in step (a); (c) conducting anaerobic digestion of the other part of the raw material, which does not contain the inhibitory materials, as well as the hydrolyzed material formed in step (b), so as to produce bio-gas; and (d) subjecting the liquid-phase material separated in step (a) and a liquid waste formed by anaerobic digestion in step (c) to membrane separation, in order to concentrate the same.

According to the present invention, before introducing a solid-phase sludge separated in the solid-liquid separator into the anaerobic digestion reactor, a solid-phase material contained in this sludge can be converted into a liquid-phase material by hydrolyzing the sludge (through high temperature, high pressure or ozone treatment, or the like). Dissolved matter (an organic material) converted into the liquid-phase material by hydrolysis, is then introduced into the anaerobic digestion reactor, in which the dissolved matter is degraded/ingested within a short time by anaerobic microorganisms to thereby enable effective and efficient production of bio-gas.

In addition, a treated solution (a leachate) containing a large amount of anaerobic microorganisms in the solid-liquid separator is introduced into a sludge concentrator (that is, a membrane separation device), followed by separation of the anaerobic microorganisms and concentration thereof to produce a concentrated sludge. Such a concentrated sludge is returned to the anaerobic digestion reactor or a raw material storage tank, thus maintaining a large amount of the anaerobic microorganisms in the anaerobic digestion reactor and enabling the microorganisms to exist therein for a long term.

BRIEF DESCRIPTION OF THE DRAWINGS

The above and other objects, features and other advantages of the present invention will be more clearly understood from the following detailed description taken in conjunction with the accompanying drawing, in which:

FIG. 1 is a schematic diagram for illustrating a structure of an apparatus for production of bio-gas according to the present invention.

DETAILED DESCRIPTION OF THE INVENTION

Hereinafter, the present invention will be described in more detail, in conjunction with the accompanying drawing.

FIG. 1 schematically illustrates a structure of an apparatus for production of bio-gas according to the present invention. The apparatus for production of bio-gas according to the present invention has a configuration in that a first solid-liquid separator 10, a hydrolysis reactor 20, an anaerobic digestion reactor 30, a second solid-liquid separator 40 and a sludge concentrator 50 are sequentially arranged.

First, a raw material, for producing bio-gas is classified into one free from inhibitory materials and the other containing the inhibitory materials, wherein the former without the inhibitory material is directly introduced into the anaerobic digestion reactor 30 while the latter containing the inhibitory materials is fed to the same anaerobic digestion reactor 30 through the first solid-liquid separator 10 and the hydrolysis reactor 20.

The first solid-liquid separator 10 separates the raw material containing the inhibitory materials into a solid-phase material (without the inhibitory materials) and a liquid-phase material (containing the inhibitory materials). The solid-phase material (without the inhibitory materials) separated from the raw material is introduced into the hydrolysis reactor 20, in which the solid-phase material is subjected to hydrolysis at a high temperature and a high pressure (or while adding an oxidizing agent thereto), and then, converted into a liquid-phase material and fed to the anaerobic digestion reactor 30.

On the other hand, the liquid-phase material (containing the inhibitory materials) separated from the raw material in the first solid-liquid separator 10 is not introduced into the anaerobic digestion reactor 30, and instead, is fed to the sludge concentrator 50 placed at the end of the apparatus, to thereby prevent a decrease in efficiency of the anaerobic digestion reactor due to the inhibitory materials.

Since a leachate (a liquid waste) of the anaerobic digestion reactor 30 contains a large amount of solids (TS 10 to 20%), in order to reduce load on the sludge concentrator 50, the liquid waste firstly enters the second solid-liquid separator 40. The second solid-liquid separator 40 conducts solid-liquid separation of the liquid waste to feed a liquid-phase material separated therefrom to the sludge concentrator 50 while discharging a dehydrated cake as a solid matter to the outside.

Consequently, only waste water with reduced load separated in the first and second solid-liquid separators 10 and 40 is introduced into the sludge concentrator 50, whereas a concentrated sludge containing anaerobic microorganisms in a large amount is returned to the anaerobic digestion reactor 30 or a raw material storage tank. On the other hand, the sludge concentrator 50 may include a membrane separation device or the like.

When the raw material containing the inhibitory material is separated in the first solid-liquid separator 10 to prepare a liquid-phase material, a dissolved organic matter is also generated. However, as shown in table 1 below, since a soluble chemical oxygen demand (SCOD) of the dissolved organic matter is considerably lower than a total chemical oxygen demand (TCOD), the dissolved organic matter may not substantially influence an amount of bio-gas to be produced. Characteristics of general organic waste are shown in table 1 and materials inhibitory to anaerobic microorganisms and concentrations thereof are shown in table 2.

TABLE 1

Characteristics of general organic waste

| Characteristic | Animal waste | Food waste |
|---|---|---|
| pH | 6.08 | 5.02 |
| TCODcr (g/L) | 164.8 | 207.6 |
| SCODcr (g/L) | 75.2 | 106.0 |
| $NH_4$—N (g/L) | 4.8 | 2.0 |
| $Cl^-$ (g/L) | 1.8 | 7.5 |

TABLE 1-continued

Characteristics of general organic waste

| Characteristic | Animal waste | Food waste |
|---|---|---|
| TS (%) | 8.5 | 14.8 |
| VS (%) | 6.9 | 13.6 |

TABLE 2

Materials inhibitory to anaerobic microorganisms and concentrations thereof

| Material | Inhibitory concentration (mg/L) |
|---|---|
| Ammonia | 1,500 |
| Arsenic | 1.6 |
| Boron | 2.0 |
| Cadmium | 0.02 |
| Chromium ($Cr^{6+}$) | 5 to 50 |
| Chromium ($Cr^{3+}$) | 50 to 500 |
| Copper | 1 to 10 |
| Cyanide | 4 |
| Iron | 5 |
| Magnesium | 1,000 |
| Sodium | 3,500 |
| Sulfide | 50 |
| Zinc | 5 to 20 |
| Alcohol, allyl | 100 |
| Alcohol, octyl | 200 |
| acrylonitrile | 5 |
| Benzidine | 5 |
| Chloroform | 10 to 16 |
| Carbon tetrachloride | 10 to 20 |
| Methylene chloride | 100 to 500 |
| 1,1,1-trichloroethane | 1 |
| Trichlorofluoromethane | 20 |
| trichlorotrifluoroethane | 5 |

In addition, as shown in table 3 below, anaerobic microorganisms have a cell production degree about 1/10 times that of aerobic microorganisms, and therefore, show higher sensitivity to inhibitory materials and require a longer stable residence time than the aerobic microorganisms.

TABLE 3

Energy efficiency and cell production degree of anaerobic microorganisms and aerobic microorganisms

| Final electron carrier molecule | Form of respiration | Pound of cells produced per pound of COD degraded |
|---|---|---|
| $O_2$ | Aerobic or oxic | 0.4 to 0.6 |
| Organic molecule | Anaerobic: mixed acids and alcohol | 0.04 to 0.1 |
| $CO_2$ | Anaerobic: methane production | 0.02 to 0.04 |

As described above, according to the present invention, since a solid-phase sludge separated in the solid-liquid separator is firstly subjected to hydrolysis (high temperature, high pressure or ozone treatment, or the like) before entering the anaerobic digestion reactor, a solid-phase material in the sludge may be converted into a liquid-phase material. A dissolved matter (an organic material) converted into a liquid-phase by hydrolysis is introduced into the anaerobic digestion reactor, in which it is degraded/ingested by anaerobic microorganisms for a short time, thereby efficiently and effectively producing bio-gas.

Since the anaerobic microorganisms may directly degrade/ingest the liquid-phase material produced during hydrolysis, a reaction rapidly proceeds leading to a reduction in a required size of the digestion reactor by about 20 to 30% and, at the same time, decreasing equipment costs. Consequently, an overall cost of facilities may be reduced by about 25 to 35%.

Furthermore, the treated liquid waste containing a large amount of anaerobic microorganisms, obtained from the solid-liquid separator is fed to the sludge concentrator (a membrane separation device), a concentrated sludge produced by separation/concentration of the anaerobic microorganisms is returned to the anaerobic digestion reactor or the raw material tank. As a result, a large amount of anaerobic microorganisms may be maintained in the anaerobic digestion reactor, in turn, residing therein for a long period of time.

Accordingly, inhibitory materials contained in a raw material are substantially removed and the raw material may have improved quality by hydrolysis. In addition, by returning a concentrated sludge containing a large amount of anaerobic microorganisms to a digestion reactor, production of bio-gas by the anaerobic microorganisms is maximized while equipment costs are decreased, thereby ensuring favorable efficiency and economic advantages.

While the present invention has been shown and described in connection with an exemplary embodiment together with the accompanying drawing, it will be apparent to those skilled in the art that the above exemplary embodiment is proposed only for illustration purpose, and modifications and variations and other equivalent embodiments can be made therefrom. Accordingly, essential technical configurations of the present invention to be protected should be defined without departing from the spirit and scope of the invention as defined by the appended claims.

What is claimed is:

1. An apparatus for producing bio-gas, comprising:
   an anaerobic digestion reactor to which a part of a raw material is fed, wherein the part does not contain inhibitory materials;
   a first solid-liquid separator to which the other part of the raw material is fed, wherein the other part contains the inhibitory materials, and which separates this part into a solid-phase material free from the inhibitory materials and a liquid-phase material containing the inhibitory materials;
   a hydrolysis reactor that executes hydrolysis of the solid-phase material obtained from the first solid-liquid separator and then feeds the treated material into the anaerobic digestion reactor; and
   a sludge concentrator that concentrates the liquid-phase material obtained from the first solid-liquid separator as well as a liquid waste of the anaerobic digestion reactor.

2. The apparatus according to claim 1, further comprising a second solid-liquid separator to execute solid-liquid separation of a digested waste fed from the anaerobic digestion reactor in order to feed the liquid-phase material to the sludge concentrator.

3. A method for producing bio-gas, comprising the steps of:
   (a) separating a part of a raw material, which contains inhibitory materials, into a solid-phase material free from the inhibitory materials and a liquid-phase material containing the inhibitory materials;
   (b) hydrolyzing the solid-phase material generated in step (a);
   (c) conducting anaerobic digestion of the other part of the raw material, which does not contain the inhibitory materials, as well as the hydrolyzed material formed in step (b), so as to produce bio-gas; and
   (d) subjecting the liquid-phase material separated in step (a) and a liquid waste formed by anaerobic digestion in step (c) to membrane separation, in order to concentrate the same.

\* \* \* \* \*